(12) United States Patent
Spehr et al.

(10) Patent No.: US 6,240,320 B1
(45) Date of Patent: *May 29, 2001

(54) CARDIAC LEAD WITH ZONE INSULATED ELECTRODES

(75) Inventors: Paul R. Spehr; James E. Machek, both of Lake Jackson; David R. Erickson, Friendswood; John A. Schmidt, Lake Jackson, all of TX (US)

(73) Assignee: Intermedics Inc., Angleton, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,106

(22) Filed: Jun. 5, 1998

(51) Int. Cl.⁷ .................................................... A61N 1/05
(52) U.S. Cl. .................................... 607/122; 607/121
(58) Field of Search ............................... 607/122, 116, 607/119, 121, 123; 600/374, 373

(56) References Cited

U.S. PATENT DOCUMENTS

| 3,911,928 | * | 10/1975 | Lagergren | 607/122 |
| 4,026,303 | * | 5/1977 | Babotai | 607/127 |

(List continued on next page.)

FOREIGN PATENT DOCUMENTS

| 054781 | 12/1980 | (EP) | A61N/1/04 |
| 0191238 | 12/1985 | (EP) | A61N/1/05 |
| 191238 | 12/1985 | (EP) | A61N/1/05 |
| 296001 | 6/1987 | (EP) | A61N/1/05 |
| 0296001 | 6/1988 | (EP) | A61N/1/05 |

(List continued on next page.)

OTHER PUBLICATIONS

Mira Mohanty et al., Long term soft tissue response to metals, ceramics and composites—a comparative histopathological evaluation, Bull. Mater. Sci., vol. 9, No. 5, pp. 309–315, 1987.

A.C. Evans et al., Diamond–like carbon applied to bioengineering materials, Surface and Coatings Technology, vol. 47, pp. 662–667, 1991.

(List continued on next page.)

Primary Examiner—Kennedy Schaetzle
(74) Attorney, Agent, or Firm—Schwegman, Lundberg, Woessner & Kluth, P.A.

(57) ABSTRACT

An electrode for a cardiac lead and method of making the same are provided. The electrode includes an electrode member and a coating applied to the electrode member. The coating is composed of an electrically insulating material and covers a first portion of the exterior of the electrode member while leaving a preselected second portion thereof exposed. The second or exposed portion enhances the impedance of the electrode, resulting in power savings and extended life spans for implantable stimulation and sensing devices. Exemplary materials for the coating includes diamond-like carbon and sapphire.

40 Claims, 7 Drawing Sheets

U.S. PATENT DOCUMENTS

| | | | |
|---|---|---|---|
| 4,044,774 | | 8/1977 | Corbin et al. .......................... 128/404 |
| 4,440,178 | * | 4/1984 | Bussard et al. ...................... 607/121 |
| 4,502,492 | * | 3/1985 | Bornzin ................................ 607/121 |
| 4,611,604 | * | 9/1986 | Botvidsson et al. ................. 607/122 |
| 4,630,611 | * | 12/1986 | King ..................................... 600/377 |
| 4,649,937 | * | 3/1987 | DeHaan et al. ...................... 607/115 |
| 4,760,852 | * | 8/1988 | Lekholm ............................... 607/116 |
| 4,765,341 | | 8/1988 | Mower et al. ........................ 128/785 |
| 5,222,506 | | 6/1993 | Patrick et al. ........................ 128/784 |
| 5,231,996 | | 8/1993 | Bardy et al. .......................... 128/785 |
| 5,324,322 | | 6/1994 | Grill, Jr. et al. ...................... 607/118 |
| 5,405,373 | * | 4/1995 | Petersson et al. .................... 607/121 |
| 5,405,375 | * | 4/1995 | Ayers et al. .......................... 607/122 |
| 5,456,254 | | 10/1995 | Pietroski et al. ..................... 128/642 |
| 5,514,173 | | 5/1996 | Rebell et al. ......................... 607/127 |
| 5,515,848 | | 5/1996 | Corbett, III et al. ................ 128/642 |
| 5,522,877 | | 6/1996 | Garfield et al. ...................... 607/138 |
| 5,579,764 | | 12/1996 | Goldreyer ............................. 128/642 |
| 5,658,321 | * | 8/1997 | Fayram et al. ......................... 607/36 |
| 5,683,443 | | 11/1997 | Munshi et al. ....................... 607/121 |
| 5,779,699 | * | 7/1998 | Lipson .................................. 607/122 |
| 5,782,900 | * | 7/1998 | De La Rama et al. .............. 607/122 |
| 5,785,706 | | 7/1998 | Bednarek .............................. 606/41 |
| 5,807,399 | | 9/1998 | Laske et al. .......................... 607/126 |
| 5,836,874 | * | 11/1998 | Swanson et al. ..................... 600/374 |
| 5,860,974 | * | 1/1999 | Abele ................................... 600/374 |
| 5,871,529 | | 2/1999 | Bartig et al. .......................... 607/122 |
| 5,871,531 | * | 2/1999 | Struble ................................. 607/126 |
| 5,871,532 | | 2/1999 | Schroeppel ........................... 607/128 |
| 5,873,894 | | 2/1999 | Vandegriff et al. ....................... 607/9 |
| 5,876,408 | | 3/1999 | Alt et al. .............................. 606/129 |
| 5,876,424 | | 3/1999 | O'Phelan et al. ....................... 607/36 |
| 5,876,431 | | 3/1999 | Spehr et al. .......................... 607/126 |
| 5,885,221 | | 3/1999 | Hsu et al. ............................. 600/515 |
| 5,908,447 | | 6/1999 | Schroeppel et al. ................. 607/126 |
| 5,913,887 | | 6/1999 | Michel ................................. 607/123 |
| 5,916,238 | | 6/1999 | Hauser et al. ........................... 607/5 |
| 5,925,069 | | 7/1999 | Graves et al. .......................... 607/36 |
| 5,925,073 | | 7/1999 | Chastain et al. ..................... 607/122 |
| 5,931,858 | | 8/1999 | Kadhiresan et al. ................. 607/20 |
| 5,931,864 | | 8/1999 | Chastain et al. ..................... 607/128 |
| 5,935,154 | | 8/1999 | Westlund .............................. 607/36 |
| 5,935,160 | | 8/1999 | Auricchio et al. ................... 607/122 |
| 5,935,465 | | 8/1999 | Cardineau et al. .................. 219/121 |
| 5,941,903 | | 8/1999 | Zhu et al. .............................. 607/13 |
| 5,941,904 | | 8/1999 | Johnston et al. ....................... 607/19 |
| 5,944,744 | | 8/1999 | Paul et al. ............................... 607/9 |
| 5,951,597 | | 9/1999 | Westlund et al. .................... 607/126 |
| 5,954,753 | | 9/1999 | Alt et al. .................................. 607/8 |
| 5,957,966 | | 9/1999 | Schroeppel et al. ................. 607/122 |
| 5,978,707 | | 11/1999 | Krig et al. .............................. 607/14 |
| 5,978,710 | | 11/1999 | Prutchi et al. ......................... 607/17 |
| 5,983,138 | | 11/1999 | Kramer .................................. 607/9 |
| 5,989,077 | | 11/1999 | Mast et al. .......................... 439/814 |

FOREIGN PATENT DOCUMENTS

| | | | |
|---|---|---|---|
| 2225179 | 3/1974 | (FR) | ................. A61N/1/04 |
| 93/00130 | 6/1991 | (WO) | ............... A61N/1/05 |
| 98/31419 | 7/1998 | (WO) | ............... A61N/1/05 |

OTHER PUBLICATIONS

I. Dion et al., Hemocompatibility of Diamond–Like Carbon Coating, Bio–Medical Materials and Engineering, vol. 3, pp. 51–55, 1993.

P.R. Chalker et al., *IEE Colloquium on Diamond in Electronics and Optics*, Digest No. 1993/204, all pages, 1993.

Matthew Allen et al., *The Effects of Diamond–like Carbon Coatings on Macrophages, Fibroblasts and Osteoblast–like Cells in vitro*, Clinical Materials 17, pp. 1–10, 1994.

N.J. Ianno, Deposition of diamond–like carbon on a titanium biomedical alloy, Thin Solid Films 270, pp. 275–278, 1995.

Ruth S. Butler, Diamond–Like Carbon for Biomedical Applications (Review), Journal of Chemical Vapor Deposition, vol. 3, pp. 182–192, 1995.

Haruyuki Kawahara, Cellular response to implant materials: biological, physical and chemical factors, International Dental Journal, pp. 350–375, 1983.

A. O'Leary et al., Diamond–like carbon coatings for biomedical applications, Key Engineering Materials, vol. 99–100, pp. 301–307, 1995.

U. Müller, et al., XPS investigation of Ti–O containing diamond–like carbon films, Thin Solid Films 290–292, pp. 323–327, 1996.

Parylene Coating Services, Inc., Properties of diX dimer—Sales Brochure, all pages, unknown.

Nova Tran Corporation, Automated Parylene Deposition System PDS–2090—Sales Brochure, all pages, unknown.

* cited by examiner

CARDIAC LEAD WITH ZONE INSULATED ELECTRODES

BACKGROUND OF THE INVENTION

1. Field of the Invention

This invention relates generally to cardiac stimulator leads, and more particularly to a cardiac stimulator lead having an electrode selectively coated with an insulating material to define small conductive regions.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

Most implantable cardiac stimulators include a circuit board enclosed within a sealed housing or can. The circuit board controls the delivery of electric pulses to the lead and may perform various other functions. Power is supplied by an internal dry cell battery or set of batteries. In some systems, the batteries may be recharged non-invasively and without excising the cardiac stimulator. However, most systems employ disposable batteries. When the disposable cells are depleted, the cardiac stimulator must be excised and replaced.

A conventional cardiac stimulator lead normally consists of an elongated flexible tubular, electrically insulating sleeve that is connected proximally to a connector that is adapted to couple to the header of a cardiac stimulator can, and distally to a tubular tip electrode. One or more ring-type electrodes may be secured to the sleeve at various positions along the length of the sleeve. The proximal end of the lead sleeve is connected to the connector by application of various biocompatible adhesives to various portions of the connector and the sleeve. The tip electrode ordinarily consists of a tubular structure that has an increased diameter portion that forms an annular shoulder against which the distal end of the lead sleeve is abutted. The exterior surface of the tubular structure is normally smooth as is the interior surface of the distal end of the lead sleeve. In multi-polar leads, one or more ring-type electrodes may be fitted over the sleeve.

To ensure that physical contact with the desired myocardial tissue is maintained after implantation, tip electrodes for most conventional leads are anchored to myocardial tissue by a fixation mechanism of one sort or another. In some leads, a corkscrew-like member projects from the tip electrode and penetrates the endocardium. In others, the electrode is fitted with one or more radially projecting tines that engage the normally irregular surface of the endocardium. Still others may employ both types of structures.

Most conventional tip electrodes serve at least two functions. In one aspect, tip electrodes provide a conducting member to convey electrical stimulation and/or sensing signals to and from myocardial tissue. In another aspect, most tip electrodes provide structure to accommodate either a directly incorporated fixation mechanism or a retrofitted fixation mechanism. Although conventional ring electrodes may be fitted with tines, most such electrodes serve primarily as signal conductors.

The design of cardiac stimulation systems involves a balancing of a number of competing design considerations. Some of these include can size, lead tip dimensions and power consumption. Can miniaturization has been an important design goal since the first implantable pacemakers were introduced over thirty years ago. Smaller cans yield better post-operative comfort and cosmetic results for the patient. However, can miniaturization has required downsizing in storage batteries, which has, in turn, placed a premium on power consumption. Power consumption is of great importance because for a given level of power consumption, smaller batteries generally translate into shorter cardiac stimulator life spans and more frequent surgical procedures for the patient.

Some of the limitations associated with diminishing battery size have been offset by advances in dry cell chemistry. In addition, advances in pulse generation circuitry have dramatically increased the efficiency of power consumption. For example, many cardiac stimulators incorporate circuitry that automatically tailors pulse generation to the physiological demands of the patient.

However, despite advances in battery chemistry and circuitry, power consumption efficiency is still frequently limited by conventional lead electrode design. Most conventional lead electrodes operate as relatively low impedance, and thus, high current drawing devices. The low impedance levels are primarily a function of the relatively large conducting surface areas that these devices present to myocardial tissue. As noted above, the size of conventional lead electrodes is dictated in large part by mechanical considerations, such as the facilitation of fixation mechanisms. Furthermore, a certain degree of bluntness in a tip electrode is desirable to reduce the risk of myocardial perforation and micro-dislodgement, and to facilitate capture of the lead tip by post-implant developing fibrous tissue. Similarly, miniaturization of ring-type electrodes is generally limited by the size of the insulating lead sleeve and by the prevailing mechanical systems used to secure such ring-type electrodes to the lead sleeve.

As a result of these mechanical design considerations, current is often drawn by conventional low impedance electrodes at higher rates than necessary for appropriate stimulation. Some improvement in current drain may be realized by lowering the voltage output of the pulse generator. However, this technique is not possible in patients who require a particular threshold voltage for successful stimulation that is above the contemplated lowered output voltage. Thus, conventional lead electrode designs may represent an impediment to extended battery life.

In one conventional lead design, the distal end of the lead is provided with a distally projecting, small diameter circular electrode that has the potential to provide enhanced pacing impedance. However, this design may be prone to micro-dislodgment. Since the lead is provided with a single small conducting surface on the distal end of the lead, normal heart motion may cause the small conducting surface to momentarily lose contact with or micro-dislodge from myocardial tissue and disrupt the flow of pacing pulses.

The present invention is directed to overcoming or reducing the effects of one or more of the foregoing disadvantages.

SUMMARY OF THE INVENTION

In accordance with one aspect of the present invention, a cardiac lead electrode is provided. The lead includes an electrode member and a coating applied to the electrode member. The coating is composed of an electrically insulating material and covers a first portion of the exterior of the electrode member while leaving a preselected second portion thereof exposed.

In accordance with another aspect of the present invention, a cardiac stimulator lead is provided. The cardiac stimulator lead includes a conductor wire that has an electrically insulating coating applied thereto and an electrode member coupled to the conductor wire. The electrode member has a coating applied thereto. The coating is composed of an electrically insulating material and covers a first portion of the exterior of the electrode member while leaving a preselected portion thereof exposed.

In accordance with another aspect of the present invention, a method of fabricating a high impedance cardiac lead electrode is provided. The method includes the steps of providing an electrode member and coating a first portion of the electrode member with an electrically insulating material while leaving a preselected second portion thereof exposed.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
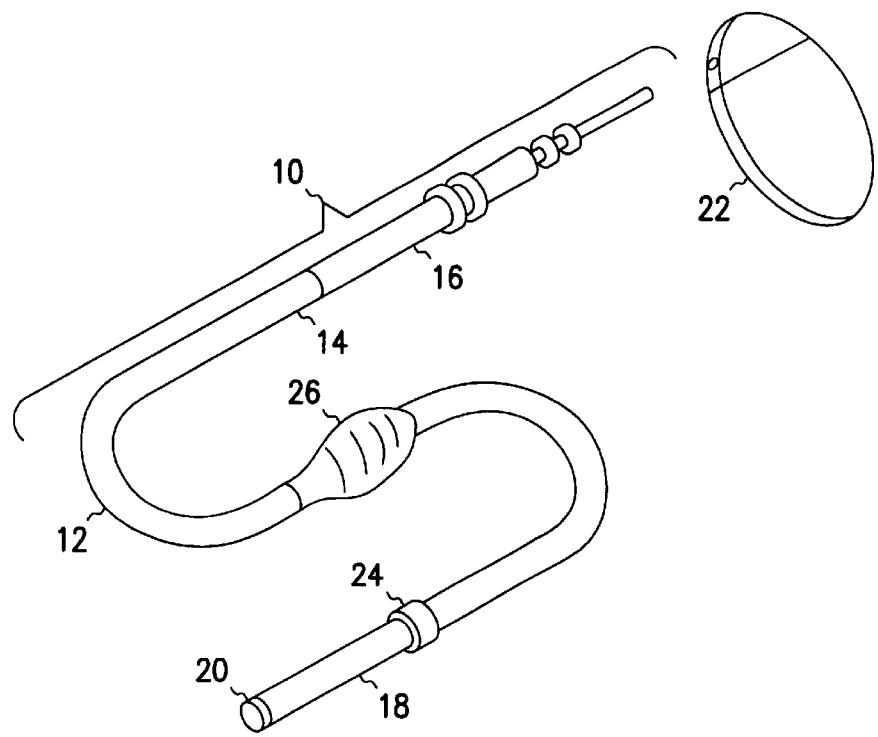
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac stimulator lead 10 that includes a flexible insulating sleeve 12 that has a proximal end 14 coupled to a connector 16, and a distal end 18 coupled to a tip electrode 20. The connector 16 is designed to be inserted into a cardiac stimulator 22, and is shown highly exaggerated in size relative to the cardiac stimulator 22. The cardiac stimulator 22 may be a pacemaker, a cardioverter/defibrillator, or other type of stimulator or a sensing instrument. The illustrated embodiment of the lead 10 is bipolar. Accordingly, the distal end 18 is provided with an electrode 24 located proximal to the tip electrode 20. However, unipolar or other multi-polar arrangements are possible as well. A suture sleeve 26 is slipped over the sleeve 12. During implantation, the suture sleeve 26 is sewn to body tissue at the site of transvenous entry.

The sleeve 12 is a flexible tubular member that provides a robust, electrically insulating coupling between the connector 16 and the electrode 20. The sleeve 12 protects one or more fine gage conductor wires enclosed therein from body fluids and tissues, and is advantageously composed of a biocompatible, electrically insulating material, such as silicone, polyurethane, or like materials.

Figure 2:
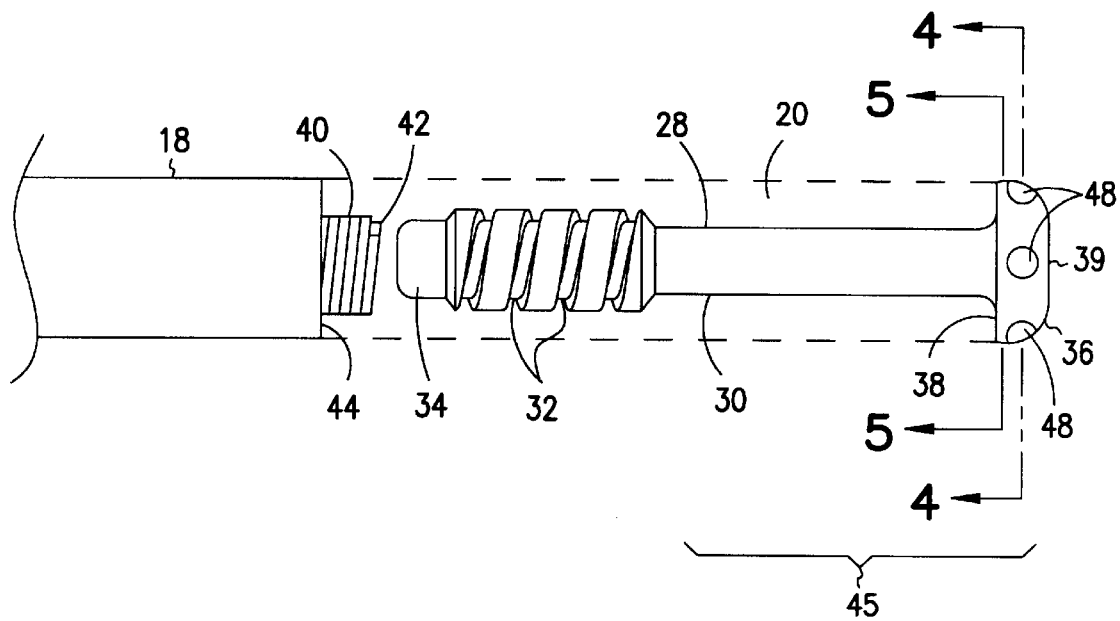
FIG. 2 is an exploded side view of an exemplary cardiac lead electrode, sleeve and conductor in accordance with the present invention.
Figure 3:
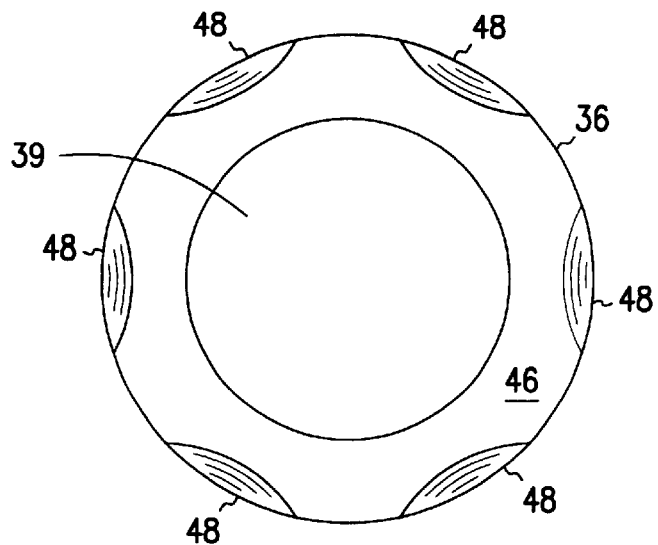
FIG. 3 is an end view of the electrode shown in FIG. 2 in accordance with the present invention.

The detailed structure of the electrode 20 may be understood by referring now also to FIG. 2, which is an exploded side view of the electrode 20 and the end 18 of the sleeve positioned distal from the electrode 24, and to FIG. 3 which is an end view of FIG. 2. The electrode 20 includes an electrode member 28 that has an elongated mandrel-like shank 30 that is provided with a set of external grooves or threads 32 at its proximal end 34 and terminates in an enlarged diameter tip 36. The grooves 32 may be formed integrally with the shank 30 or machined as a separate structure that may be welded or otherwise connected to the shank 30. The transition from the shank 30 to the larger diameter tip 36 defines a proximally facing annular shoulder 38. The tip 36 has a profile that tapers inwardly to a circular blunt or flat end surface 39. Although the profile of the tip 36 is largely a matter of design discretion, an overall blunt profile of the distal end of the tip 36 reduces the potential for myocardial penetration and micro-dislodgment.

The electrode member 28 is advantageously fabricated from a biocompatible conductor or semiconductor material. Suitable materials include, for example, iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material. A portion of the electrode 20 may be composed of other than a conducting material so long as a conducting pathway is provided between the conductor wire 40 and the tip 36.

A conductor wire 40, shown exploded from the electrode 20, is slipped over the proximal end 34 of the shank 30 and spiraled around the grooves 32 when the lead 10 is assembled. The wire 40 is depicted as a coiled metallic conductor wire that is individually insulated with a thin insulating jacket. An end 44 of the wire 40 is stripped as shown to establish a good electrical contact with the exterior of the shank 30. The end 44 may also be spot welded by laser or other suitable techniques to the exterior of the shank 30. The proximal end of the wire 40 is coupled to the connector 16 shown in FIG. 1. A second conductor wire (not shown) is nested with the conductor wire 40 and is coupled distally to the annular electrode 24 and proximally to the connector 16, and is positioned in a nested arrangement with the wire 40 within the sleeve 12. The skilled artisan will appreciate that other wiring arrangements may be incorporated in lieu of the individually insulated wire 44 and the companion wire (not shown). For example, commonly used coaxial wiring arrangements may be incorporated where the individual wire coils are separated by an inner elongated tubular insulating sleeve.

When the lead 10 is fully assembled, the distal end 18 is slipped over the shank 30 until a distally facing annular shoulder 44 on the distal end 18 abuts the proximally facing annular shoulder 38 of the tip 36. A suitable medical grade, biocompatible adhesive may be applied to the exterior of the shank 30 and/or the interior of the distal end 18 to secure the distal end 18 to the electrode member 28. The adhesive may be a silicone based adhesive, or one of a variety of commercially available two stage biocompatible adhesives.

As noted above, a low impedance electrode in a cardiac lead can result in power consumption that is beyond the rate necessary for medically indicated cardiac stimulation and/or sensing. Although power supply depletion is inevitable in disposable and rechargeable self-contained storage cells, unnecessarily excessive power consumption represents a real limit on battery life. However, in accordance with the present invention, the electrode 20 may be fabricated with a higher impedance than would otherwise be possible in view of the conducting nature and structural requirements of the electrode 20. A lead fitted with the electrode 20 in accordance with the present invention may reduce power consumption and prolong battery life for the cardiac stimulator 22 without sacrificing stimulation and/or sensing functions.

Figure 4:
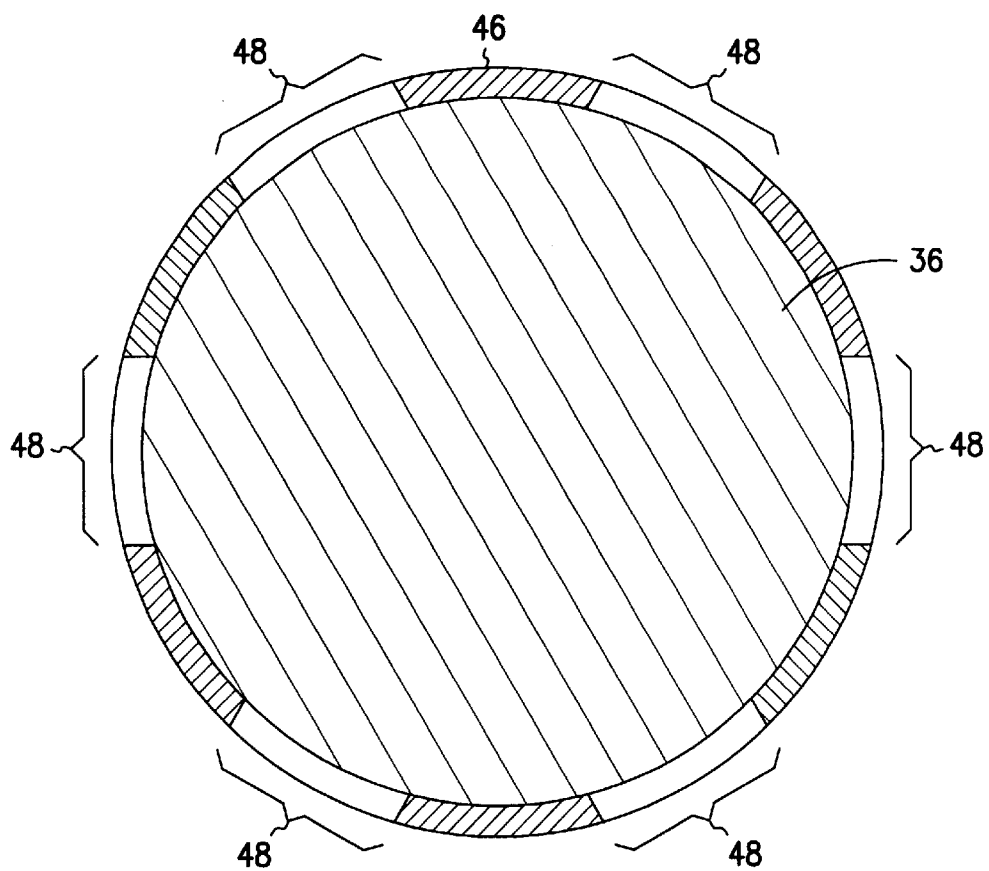
FIG. 4 is a cross-sectional view of FIG. 2 taken at section 4—4 in accordance with the present invention.
Figure 5:
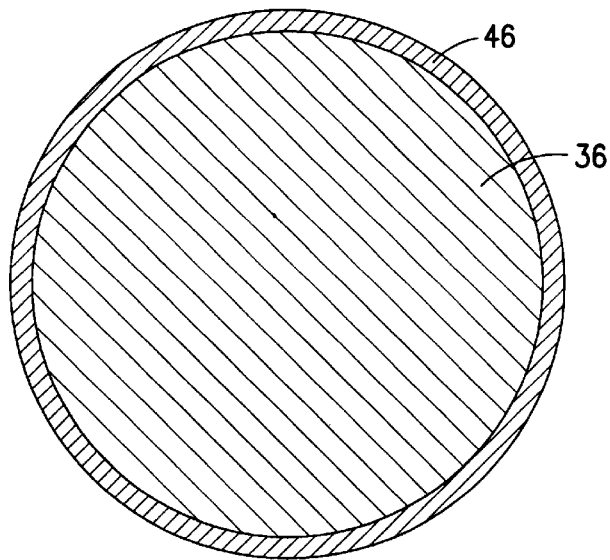
FIG. 5 is a cross-sectional view like FIG. 4 showing the electrode prior to coating with an insulating material in accordance with the present invention.

The impedance enhanced character of the electrode 20 may be understood now by referring to FIGS. 2, 3, 4, and 5. Relative to FIG. 2, FIG. 3 is an end view, and FIGS. 4 and 5 are sectional views taken, respectively, at sections 4—4 and 5—5. A first portion 45 of the exterior of the electrode member 28 from the distal end of the grooves 32 to the end 39 of the tip 36 is covered by a coating 46 composed of an electrically insulating material. A preselected second portion of the exterior of the electrode member 28 consisting of six peripherally spaced, circular spots 48 on the tip 36 is left exposed. The coating 46 substantially reduces the otherwise available conducting surface area of the electrode member 28. The exposed circular areas 48 provide small conducting surfaces to contact and transmit electrical current between the electrode 20 and myocardial tissue. The reduced surface area of the electrode member 28 that may be exposed to myocardial tissue dramatically increases the impedance of the electrode 20, thus lowering the power consumption of the lead 10, and increasing the operating life of the power supply for the cardiac stimulator 22 shown in FIG. 1.

In the embodiment illustrated in FIGS. 2, 3, 4, and 5, the first portion 45 of the electrode member 28 includes all of the exterior of the electrode member 28, save the exposed areas 48, the grooves 32, and the proximal end 34. This configuration is illustrative as the desired increase in electrode impedance may be realized when the coating 46 is applied to at least the portion of the electrode member 28 that will be in contact with myocardial tissue. The skilled artisan will appreciate that enhanced impedance may also be achieved by covering a greater or a lesser amount of the exterior of the electrode member 28. For example, the grooves 32 may also be coated if provision is made to establish a conducting connection between the stripped end 42 of the wire 40 and the grooves 32. Conversely, the coating 46 may be applied only to the portion of the electrode member 28 that will contact myocardial tissue, i.e., the tip 36, exclusive of the proximally facing annular shoulder 38.

Figure 6:
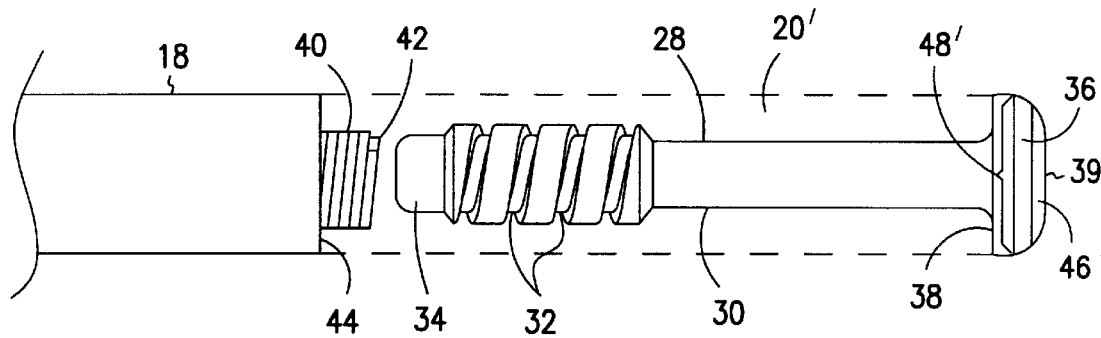
FIG. 6 is an exploded side view like FIG. 2 of an alternate exemplary electrode in accordance with the present invention.

The size, and configuration of the portion of the exterior of the electrode member 28 that is exposed following application of the coating 46 is largely a matter of design discretion and will depend on factors such as the electrical requirements of the cardiac stimulator and the medically indicated stimulation voltage, among others. For example, as shown in FIG. 6, which is a side view of an alternate embodiment of the electrode, now designated 20', the second portion, now designated 48', of the electrode member 28 that is exposed following application of the coating 46 is configured in the shape of an annular band as shown.

Figure 7:
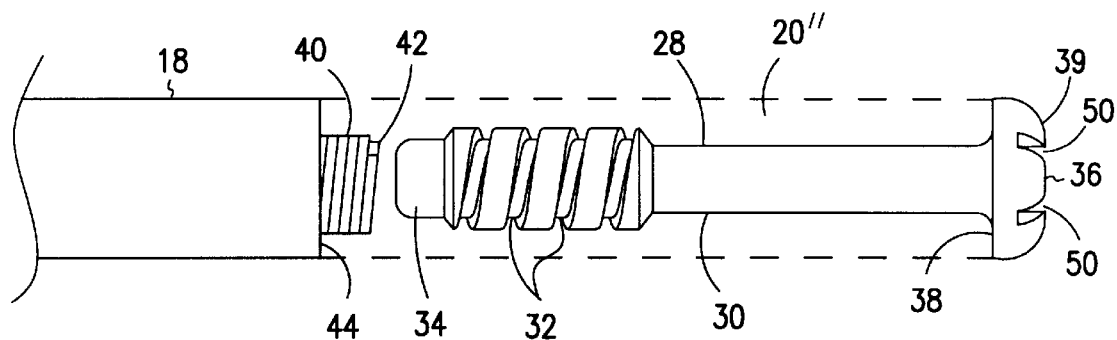
FIG. 7 is an exploded side view like FIG. 2 of another alternate exemplary electrode in accordance with the present invention.
Figure 8:
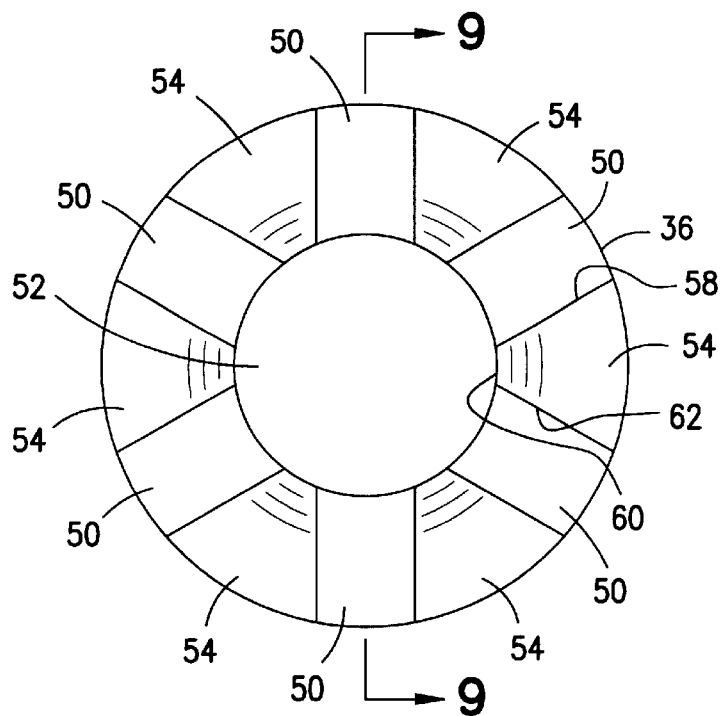
FIG. 8 is an end view of the electrode depicted in FIG. 7 in accordance with the present invention.
Figure 9:
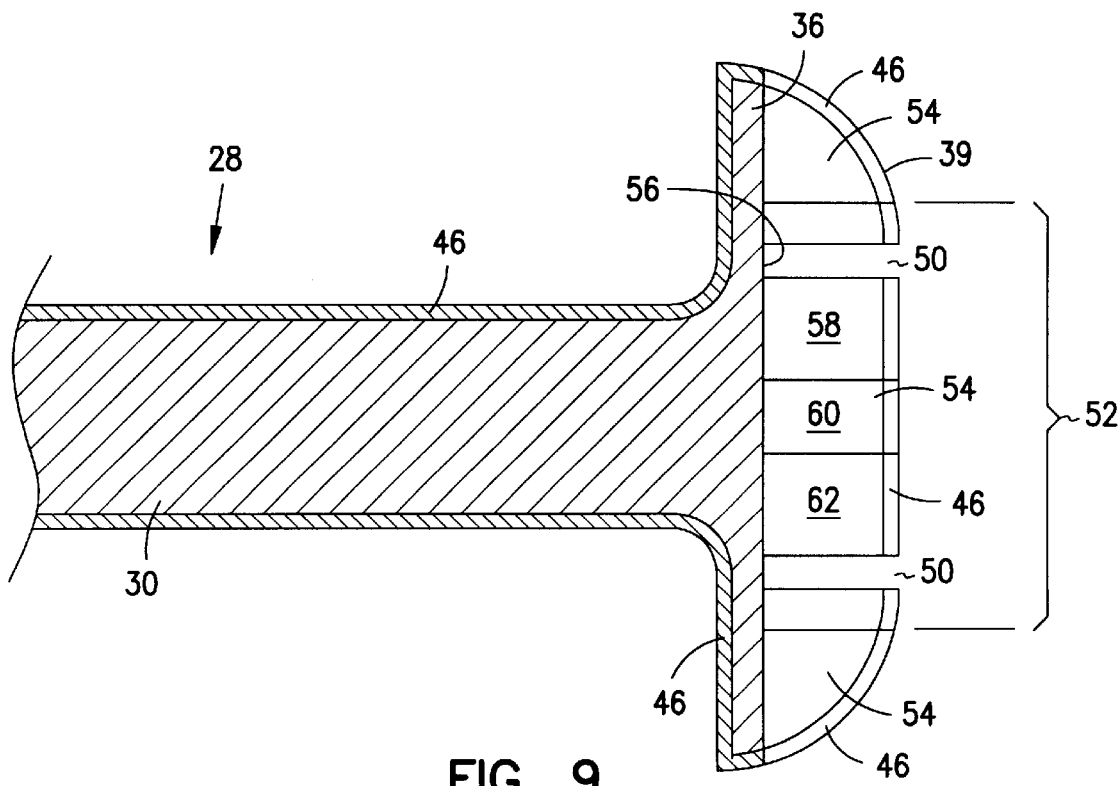
FIG. 9 is a cross-sectional view of FIG. 8 taken at section 9—9 in accordance with the present invention.

The structure of another alternate embodiment of the electrode, now designated 20", may be understood by referring now to FIGS. 7 and 8, which are, respectively, an exploded side view and an end view of the electrode 20", and to FIG. 9, which is a sectional view of FIG. 8 taken at section 9—9. In this embodiment, the tip 36 of the electrode member 28 is provided with six peripherally spaced slots 50 that commonly intersect a circular bore 52. The slots 50 divide the tip 36 into a corresponding number of peripherally spaced projections 54. In this illustrated embodiment, the second portion, that is, the portion of the exterior of the electrode member 28 that is not covered by the coating 46 includes the slots 50. Thus, the coating 46 shrouds the exterior of the projections 54 but does not coat either the bottom 56 or the vertical sidewalls 58, 60, and 62 of each projection 54. Alternatively, the projections 54 may be left exposed while the slots 50 may be shrouded by the coating 46. In either case, the design goal of reducing the exposed surface area of the electrode member 28, and thus elevating the impedance of the electrode member 28 is enhanced.

The coating 46 is advantageously composed of an electrically insulating, biocompatible material that may conformally coat the exterior of the electrode member 28. Relatively high surface and volume resistivities and dielectric strength are desirable to maintain acceptably low leakage currents and risk of dielectric breakdown. In addition, the material should exhibit good adhesion to the electrode member 28. Exemplary materials include diamond-like carbon ("DLC"), sapphire ($Al_2O_2$), parylene compounds, diamond, or like materials. The term DLC is intended to cover plasma deposited carbon films which are amorphous in structure.

The system used to apply the coating 46 will depend upon the particular material. For example, DLC and sapphire coatings may be applied by plasma enhanced chemical vapor deposition ("PECVD"), by DC reactive magnetron sputtering, or like techniques. In PECVD of DLC, a gaseous hydrocarbon, such as, methane, propane, butane, or like compounds, is introduced into the plasma chamber. As the gas interacts with the plasma, a coating of DLC forms on the targeted substrate. The deposition is advantageously carried out in the presence of one or more inert carrier gases, such as, argon, helium, or like gases. In addition to PECVD, laser induced CVD, microwave plasma assisted CVD, dual ion beam, and direct introduction of hydrocarbon gas into a saddle field source may be used as alternate techniques to apply the coating 46.

Polymeric coatings, such as parylene compounds, may be applied using a tool appropriate for the particular material. For example, Parylene C may be applied using a parylene vacuum deposition system which delivers poly-paraxylylene into a vacuum chamber containing the targeted structure, e.g., the electrode member 28.

Figure 10:
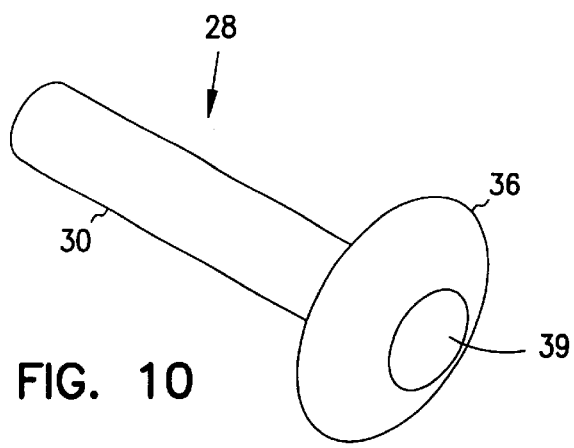
FIG. 10 is a pictorial view of a portion of an exemplary electrode prior to coating in accordance with the present invention.
Figure 11:
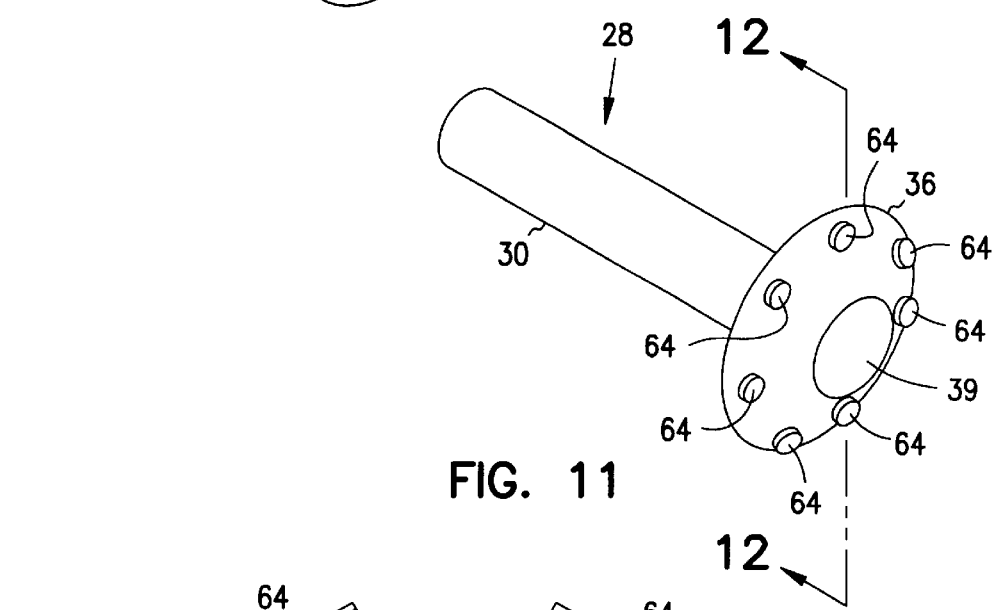
FIG. 11 is a pictorial view as in FIG. 10 with a mask applied to the electrode member.
Figure 12:
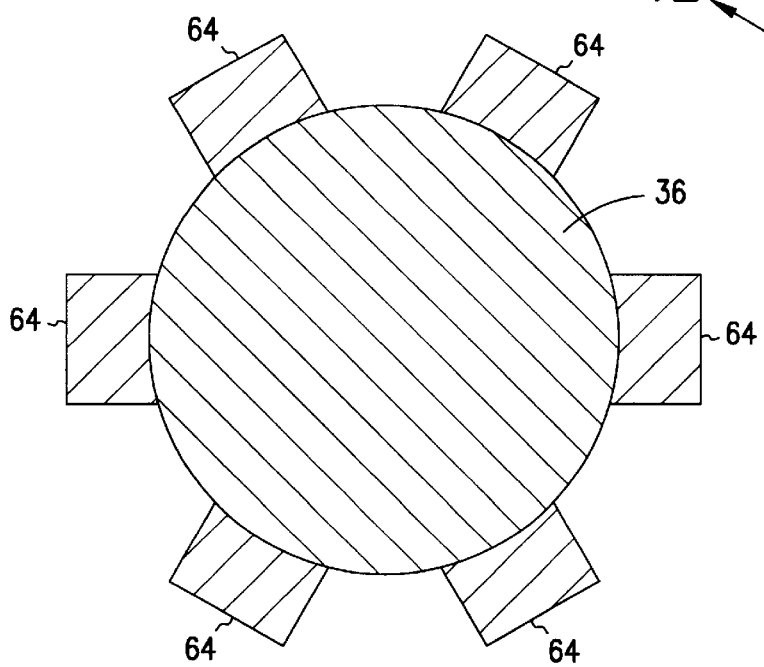
FIG. 12 is a cross-sectional view of FIG. 11 taken at section 11—11 in accordance with the present invention.

A process of applying the coating 46 to the electrode member 28 may be understood by referring now to FIGS. 10, 11, and 12. FIG. 10 is a cross-sectional view like FIG. 4, but depicts the electrode member 28 prior to the application of the coating 46 shown in FIG. 4. At this stage, an intermediary coating, such as iridium oxide, may be applied to the electrode member as desired. As shown in FIG. 11, a mask is applied over a portion of the exterior of the electrode member 28 to cover those areas of the electrode member 28 that will constitute the second portion thereof, that is, the portion of the exterior of the electrode member 28 that will remain exposed following application of the coating 46. The mask consists of individual masks 64 which cover the surface area of the electrode member tip 36 that will eventually constitute the exposed portions. The geometrical configuration of the mask will depend upon the area to be masked against the application of the coating 46. However, if a different exposed area of the electrode member 28 is desired, the mask may be shaped appropriately. A variety of materials may be used to form the mask. For example, photoresist materials commonly used in semiconductor processing may be applied, patterned, and developed using well known photolithographic patterning techniques.

Alternatively, the mask material may be a carbon paint or a ceramic material that is capable of withstanding the application process used to apply the coating 46. Such materials may be applied as small blobs by a fine gauge nozzle or other suitable dispenser. This technique may be suitable where precision crafting of the exposed areas 48 is not required.

Figure 13:
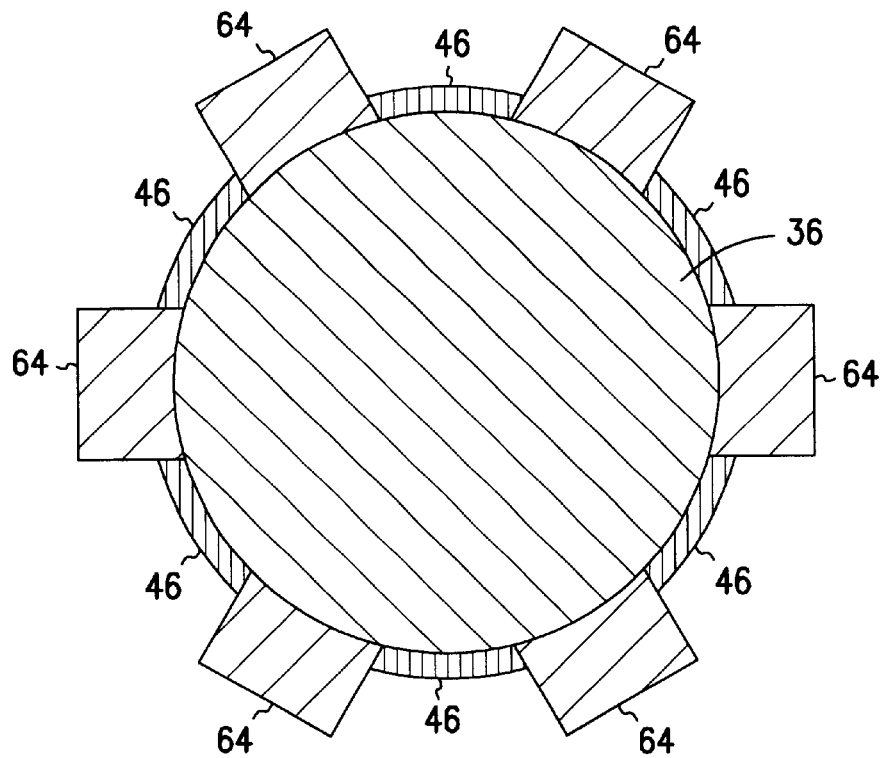
FIG. 13 is a view like FIG. 12 depicting formation of an insulating coating in accordance with the present invention.

As shown in FIG. 13, following application of the masks 64, the coating 46 is applied using a technique appropriate for the material selected. In an exemplary embodiment, the material is DLC deposited by PECVD. Following application of the coating 46, the masks 64 may be stripped to yield the structure shown in FIGS. 2, 3, and 4. If the masks 64 are composed of photoresist, well known photoresist stripping techniques may be employed. If carbon paint is used, the electrode member 28 may be sonicated in isopropyl alcohol to remove the masks 64.

The thickness of the coating 46 will depend upon the electrical requirements for the electrode 20 as well as the insulating properties of the material selected. For example, diamond-like carbon with a dielectric strength of approximately 20MV/m may be applied to a thickness of about 1.0 $\mu$m on an electrode 20 designed to operate at 1.0 volt. Sapphire, with a dielectric strength of 1.6 MV/m may be similarly applied to a thickness of about 5.0 $\mu$m.

The foregoing process flow will be substantially identical in circumstances where a different shape is desired for the exposed portion of the electrode member 28. For example, referring again to FIGS. 6 and 7, the portion 48' shown in FIG. 6 and the slots 50 shown in FIG. 7 may be left exposed following application of the coating 46 by configuring a mask in the shape of the annular band 48' or the slots 50 as the case may be. The coating 46 may then be applied as described above.

Figure 14:
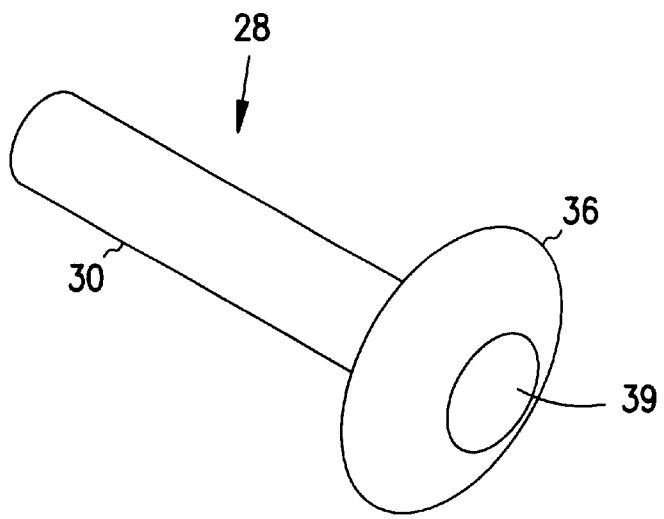
FIG. 14 is a pictorial view of a portion of an exemplary electrode depicting an alternate process for applying a coating in accordance with the present invention.
Figure 15:
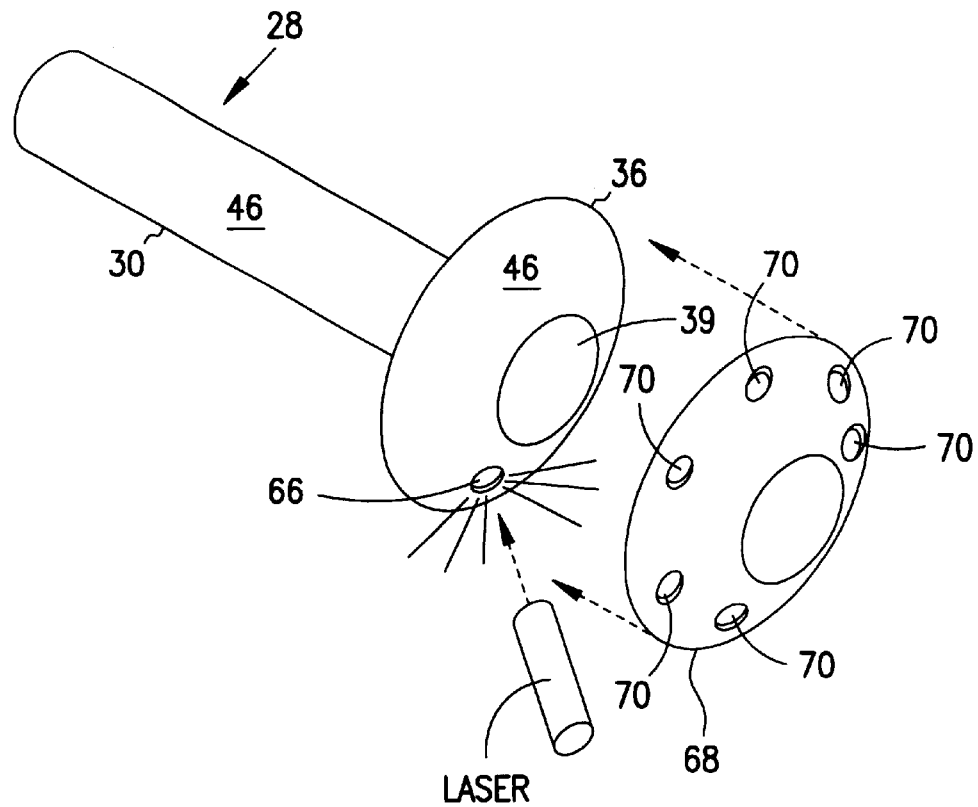
FIG. 15 is a pictorial view of the electrode shown in FIG. 14 depicting selective removal of portions of the coating to expose a preselected portion of the electrode member in accordance with the present invention.

An alternative process flow for exposing portions of the electrode member 28 may be understood by referring now to FIGS. 14 and 15. FIG. 14 is a pictorial view of a portion of the electrode member 28 and depicts deposition of a coating material on the electrode member 28. The deposition may be by any of the aforementioned techniques and will depend on the particular material selected. FIG. 15 depicts the electrode member 28 after application of the coating 46. As shown in FIG. 15, following application of the coating 46, selected portions of the coating 46 may be removed to expose the underlying areas 66 of the electrode member tip 36. The removal may be by laser ablation as depicted in FIG. 15, or by abrasive blasting, numerically controlled drill, plasma etching, or like techniques. Some removal of the underlying tip 36 is anticipated during the selective removal of the coating 46.

The technique of locating the portions 66 will depend on the removal method. If NC drilling is employed, the positions of the portions 66 may be programmed into the NC drilling apparatus. Where laser ablation is used, either the laser or the stage or chuck holding the electrode member 28, or both, may be spatially manipulated to target the laser beam. However, if abrasive blasting or plasma etching are used, a stencil sleeve 68 should be temporarily slipped over the targeted area prior to blasting or etching to mask the electrode member 28. Plasma etching may be suitable where a parylene compound is used for the coating 46. The stencil sleeve 68 includes a preselected pattern of openings 70 corresponding to the preselected pattern of portions 66. The sleeve should be composed of a material that will withstand the removal process while protecting those portions of the coating 46 that are intended to remain intact.

Figure 16:
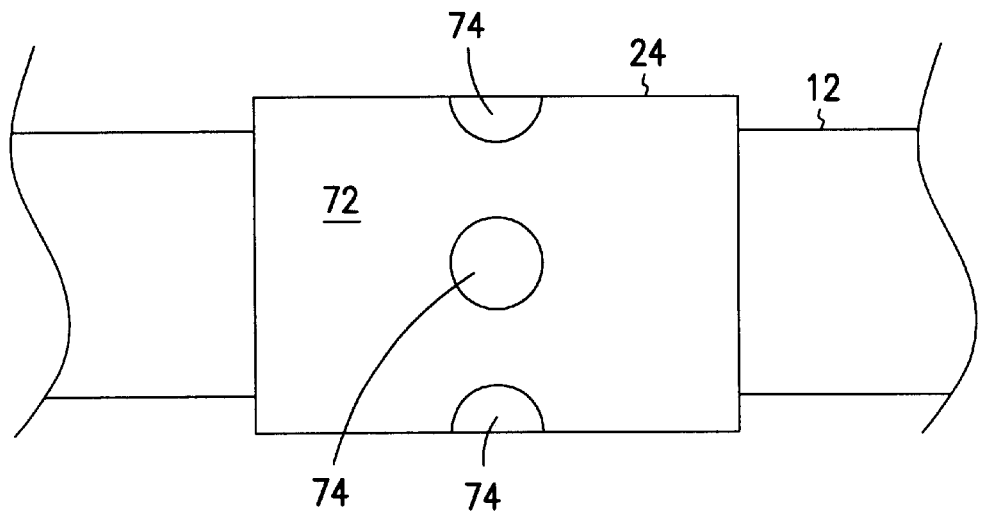
FIG. 16 is a side view of the annular electrode shown in FIG. 1 in accordance with the present invention.

As with the tip electrode 20 described above, the impedance of the annular electrode 24 shown in FIG. 1 may be enhanced. Referring now to FIG. 16, which is a magnified side view of the annular electrode 24 and a portion of the lead sleeve 12, a first portion of the annular electrode 24 may be selectively coated with a coating 72 like the coating 46, while a preselected second portion of the exterior of the electrode may be left exposed. In the illustrated embodiment, the second portion constitutes a series of peripherally spaced patches 74. However, as noted above, the configuration of the exposed area or areas may be varied. The patches 74 may be established as described above in conjunction with the electrode 20. The patches 74 provide conducting pathways to myocardial tissue with higher impedances than would otherwise be possible if the entirety of the exterior of the electrode 74 contacted myocardial tissue.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives failing within the spirit and scope of the invention as defined by the following appended claims.

What is claimed is:

1. A cardiac lead electrode, comprising:
    an electrode member including an elongate tubular shank for connecting to an end of a cardiac lead sleeve, an annular member for coupling to the exterior of a cardiac lead sleeve and a distal enlarged diameter tip with a circular, flat end surface, the distal tip having an overall blunt profile and peripherally spaced slots that define peripherally spaced projections; and a coating applied to the electrode member, the coating being composed of an electrically insulating material and covering a first portion of the exterior of the electrode member while leaving a preselected portion thereof exposed.

2. The cardiac lead electrode of claim 1, wherein the material comprises diamond.

3. The cardiac lead electrode of claim 1, wherein the material comprises sapphire.

4. The cardiac lead electrode of claim 1, wherein the material comprises parylene C.

5. The cardiac lead electrode of claim 1, wherein the whole of the electrode member is composed of a conducting material.

6. The cardiac lead electrode of claim 5, wherein the conducting material comprises iridium oxide coated titanium.

7. The cardiac lead electrode of claim 1, wherein a portion of the electrode member including the preselected portion of the exterior thereof is composed of a conducting material.

8. The cardiac lead electrode of claim 7, wherein the portion of the electrode member comprises iridium oxide coated titanium.

9. The cardiac lead electrode of claim 1, where the preselected portion comprises a plurality of circular areas.

10. A cardiac stimulator lead comprising:

a conductor wire having an electrically insulating coating applied thereto;

a connector for coupling the conductor wire to a cardiac stimulator;

a tubular insulating cardiac lead sleeve disposed around the conductor wire and coupled to the electrode member and the connector; and an electrode member coupled to the conductor wire, the electrode member comprising an elongate tubular shank for connecting to an end of the cardiac lead sleeve, an annular member for coupling to the exterior of the cardiac lead sleeve and a distal enlarged diameter tip with a circular, flat end surface, the distal tip having an overall blunt profile and peripherally spaced slots that define peripherally spaced projections, the electrode member further having a coating applied thereto, the coating being composed of an electrically insulating material and covering a first portion of the exterior of the electrode member while leaving a preselected portion thereof exposed.

11. The cardiac lead electrode of claim 10, wherein the material comprises diamond.

12. The cardiac lead electrode of claim 10, wherein the material comprises sapphire.

13. The cardiac lead electrode of claim 10, wherein the material comprises parylene C.

14. The cardiac lead electrode of claim 10, wherein the whole of the electrode member is composed of a conducting material.

15. The cardiac lead electrode of claim 14, wherein the conducting material comprises iridium oxide coated titanium.

16. The cardiac lead electrode of claim 10, wherein a portion of the electrode member including the preselected portion of the exterior thereof is composed of a conducting material.

17. The cardiac lead electrode of claim 16, wherein the portion of the electrode member comprises iridium oxide coated titanium.

18. The cardiac lead electrode of claim 10, where the preselected portion comprises a plurality of circular areas.

19. A method of fabricating a high impedance cardiac lead electrode, comprising the steps of:

providing an electrode member comprising an elongate tubular shank for connecting to an end of a cardiac lead sleeve, an annular member for coupling to the exterior of a cardiac lead sleeve and a distal enlarged diameter tip with a circular, flat end surface, the distal tip having an overall blunt profile and peripherally spaced slots that define peripherally spaced projections; and coating a first portion of the electrode member with an electrically insulating material while leaving a preselected second portion thereof exposed.

20. The method of claim 19, wherein the electrically insulating material comprises diamond.

21. The method of claim 19, wherein the electrically insulating material comprises sapphire.

22. The method of claim 19, wherein the electrically insulating material comprises parylene C.

23. The method of claim 19, wherein the step of coating the electrode member comprises applying a mask over the preselected second portion, applying the coating of the electrically insulating material, and removing the mask to expose the preselected second portion.

24. The method of claim 23, wherein the mask comprises a photoresist.

25. The method of claim 19, wherein the step of coating the electrode member comprises applying the coating of the electrically insulating material and removing a portion of the coating covering the preselected second portion of the exterior of the electrode member.

26. The method of claim 25, wherein the portion of the coating is removed by laser ablation.

27. The method of claim 25, wherein the portion of the coating is removed by mechanical drilling.

28. The method of claim 25, wherein the step of removing the portion of the coating comprises slipping a stencil sleeve over the electrode member, the sleeve comprising a stencil that exposes a portion of the coating corresponding to the preselected second portion of the exterior of the electrode member, etching the portion of the coating exposed by the stencil, and removing the sleeve.

29. The method of claim 19, wherein the electrically insulating material is applied by chemical vapor deposition.

30. The method of claim 19, wherein the electrically insulating material is applied by plasma deposition.

31. The method of claim 19, comprising the step of coating the electrode member with iridium oxide.

32. The cardiac lead electrode of claim 1 wherein the elongated tubular shank of the electrode member further comprises a set of external threads at a proximal end thereof.

33. The cardiac stimulator lead of claim 10 wherein the electrode member further comprises a set of external threads at a proximal end thereof.

34. The method of claim 19 wherein the electrode member provided further comprises a set of external threads at a proximal end thereof.

35. A cardiac lead electrode, comprising:

an electrode member including an elongated tubular shank for connecting to an end of a cardiac lead sleeve, an annular member for coupling to the exterior of a cardiac lead sleeve and a distal enlarged diameter tip with a circular, flat end surface, the distal tip having an overall blunt profile and peripherally spaced slots that define peripherally spaced projections, the distal tip being of an enlarged diameter relative to the elongated tubular shank, the elongated tubular shank being of a substantially longer length than the enlarged diameter tip, and the annular member being defined by a transition from the elongated tubular shank to the enlarged diameter tip; and a coating applied to the electrode member, the coating being composed of an electrically insulating material and covering a first portion of the exterior of the electrode member while leaving a preselected portion thereof exposed.

36. A cardiac stimulator lead comprising:

a conductor wire having an electrically insulating coating applied thereto;

a connector for coupling the conductor wire to a cardiac stimulator;

a tubular insulating cardiac lead sleeve disposed around the conductor wire and coupled to the electrode member and the connector; and an electrode member coupled to the conductor wire, the electrode member comprising an elongated tubular shank for connecting to an end of the cardiac lead sleeve, an annular member for coupling to the exterior of the cardiac lead sleeve and a distal enlarged diameter tip with a circular, flat end surface, the distal tip having an overall blunt profile and peripherally spaced slots that define peripherally spaced projections, the distal tip being of an enlarged diameter relative to the elongated tubular shank, and the elongated tubular shank being of a substantially longer length than the enlarged diameter tip, and the annular member being defined by a transition from the elongated tubular shank to the enlarged diameter tip, the electrode member further having a coating applied thereto, the coating being composed of an electrically insulating material and covering a first portion of the exterior of the electrode member while leaving a preselected portion thereof exposed.

37. A method of fabricating a high impedance cardiac lead electrode, comprising:

providing an electrode member comprising an elongated tubular shank for connecting to an end of a cardiac lead sleeve, an annular member for coupling to the exterior of a cardiac lead sleeve and a distal enlarged diameter tip with a circular, flat end surface, the distal tip having an overall blunt profile and peripherally spaced slots that define peripherally spaced projections, the distal tip being of an enlarged diameter relative to the elongated tubular shank, and the elongated tubular shank being of a substantially longer length than the enlarged diameter tip, and the annular member being defined by a transition from the elongated tubular shank to the enlarged diameter tip; and coating a first portion of the electrode member with an electrically insulating material while leaving a preselected second portion thereof exposed.

38. The cardiac lead electrode of claim 1, wherein the peripherally spaced slots commonly intersect a circular bore in distal enlarged diameter tip.

39. The cardiac lead electrode of claim 1, wherein the first portion of the electrode member is the peripherally spaced projections and the preselected portion is the peripherally spaced slots.

40. The cardiac lead electrode of claim 1, wherein the first portion of the electrode member is the peripherally spaced slots and the preselected portion is the peripherally spaced projections.

* * * * *